(12) United States Patent
O'Lenick, Jr.

(10) Patent No.: US 6,365,774 B1
(45) Date of Patent: Apr. 2, 2002

(54) CARBOXYLATED SURFACTANTS

(75) Inventor: Anthony J. O'Lenick, Jr., Dacula, GA (US)

(73) Assignee: Applied Carbo Chemicals Inc., E. Lansing, MI (US)

( * ) Notice: Subject to any disclaimer, the term of this patent is extended or adjusted under 35 U.S.C. 154(b) by 0 days.

(21) Appl. No.: 09/611,814

(22) Filed: Jul. 7, 2000

Related U.S. Application Data

(63) Continuation-in-part of application No. 09/493,172, filed on Jan. 28, 2000.

(51) Int. Cl.⁷ .................. B01F 17/44; C07C 59/305; C11D 7/26
(52) U.S. Cl. .................. 562/583; 424/70.22; 510/434; 510/479; 510/533; 516/19; 516/75; 526/911
(58) Field of Search .................. 516/75, 19; 510/434, 510/533; 562/583; 526/911; 424/70.22

(56) References Cited

U.S. PATENT DOCUMENTS

| | | | |
|---|---|---|---|
| 2,183,853 A | | 12/1939 | Haussmann et al. |
| 2,192,907 A | * | 3/1940 | Harris .................. 510/479 X |
| 2,942,013 A | * | 6/1960 | Bruson et al. ............ 516/75 X |
| 3,594,409 A | * | 7/1971 | Lachampt et al. ........ 516/75 X |
| 3,954,858 A | * | 5/1976 | Lamberti et al. .......... 562/583 |
| 4,152,515 A | * | 5/1979 | Lamberti et al. ....... 510/479 X |
| 4,654,159 A | * | 3/1987 | Bush et al. ............. 510/479 X |
| 4,827,028 A | * | 5/1989 | Scardera et al. ........ 510/479 X |
| 5,739,092 A | * | 4/1998 | Ofosu-Asante ......... 510/434 X |

* cited by examiner

Primary Examiner—Richard D. Lovering

(57) ABSTRACT

The present invention relates to a (a) dicarboxylated surfactant, (b) a method for its preparation and (c) application in industrial and personal care applications. The compounds of the present invention are made by reacting epoxy succinic acid and a salt of an alkyl non-ionic surfactant. The resulting compounds are quite stable and offer excellent emulsification properties.

19 Claims, No Drawings

CARBOXYLATED SURFACTANTS

RELATED APPLICATION

This application is a continuation in part of copending application Ser. No. 09/493,172 filed Jan. 28, 2000.

BACKGROUND OF THE INVENTION

(1) Field of Invention

The present invention relates to a (a) novel dicarboxylated surfactant, (b) a method for the preparation of said dicarboxylated surfactant and (c) application of said dicarboxylated surfactants in industrial and personal care applications.

The compounds of the present invention are made by reacting epoxy succinic acid and a salt of an alkyl alkoxylated surfactant, followed by neutralization in aqueous solution, if desired. The resulting compound is quite stable very mild to hair and skin and offers excellent surfactant properties, including detergency and foam. In addition, compounds of the present invention containing a pendant hydroxyl group which alters the water solubility and emulsification properties of the compound.

(2) Object of the Invention

It is the object of the present invention to provide novel a process for the preparation of surface active agents that are well tolerated by skin and eyes. These non-irritating products produce copious foam, have outstanding emulsification properties and are ideal products for use in the formulation of hair and skin care products like shampoos, conditioners and body washes.

(3) Description of the Arts and Practices

U.S. Pat. No. 4,065,475 to Hosi et al issued in December of 1977 discloses a process for preparation of cis epoxy succinic acid, a raw material for the preparation of the compounds of the present invention. This material is easily made by the reaction of maleic acid with hydrogen peroxide in the presence of a tungsten catalyst. The availability of this high purity raw material is very critical in the preparation of the compounds of the present invention.

THE INVENTION

SUMMARY OF THE INVENTION

The compounds of the present invention are made by reacting cis epoxy succinic acid with a salt of an alkyl alkoxylated surfactant, followed by neutralization in aqueous solution if desired. The resulting compound is an outstanding surfactant for personal care applications.

DETAILED DESCRIPTION OF THE INVENTION

The compounds of the present invention have several key portions in the molecule. Those groups include (a) an alkyl group, (b) a hydroxy linkage group and (c) two carboxy groups that improve water solubility and emulsification properties. These groups and their positioning in the molecule result in unique properties for the molecule. These include foam, detergency, chelation properties (especially for calcium ion), emulsification properties, wetting properties, particularly for hydrophobic pigments, and a lubricious skin feel. This combination of properties has heretofore been unattainable in one molecule.

Compounds of the invention conform to the following structure:

$$(R1)-CH-CH(OH)-C(O)-O^-M^+$$
$$\phantom{(R1)-CH}|$$
$$\phantom{(R1)-}C(O)-O^- \quad M^+$$

wherein;

$R^1$ is $CH_3(CH_2)_s-O-(CH_2CH_2-O)_z-(CH_2CH(CH_3)O)_y-(CH_2CH_2-O)_x$;

s is an integer ranging from 3 to 21;

x, y and z are independently integers ranging from 0 to 20 with the proviso that x+y+z equal at least 1;

M is selected from the group consisting of H, Na, K, Li, and $NH_4$.

Illustrative of the sequence for the preparation of the compounds of the present is as follows;

3 moles of sodium methylate (25% in methanol) is added to a mixture of 1 mole of alkoxylated non-ionic surfactant and one mole of epoxy succinic acid. This results in the formation of the indicated salts and the formation of the alkoxide ion of the non-ionic. The alkoxide ion reacts to open the epoxide.

$$CH_3(CH_2)_{11}(CH_2CH_2O)_7-H + 3CH_3ONa \rightarrow \text{sodium methylate}$$

$$CH_3(CH_2)_{11}(CH_2CH_2O)_7{}^-Na^+ + 3\ CH_3OH \text{ Alkoxide ion}$$

$$Na^\oplus\ {}^\ominus O-C(O)-\overset{O}{\overset{/\backslash}{CH-CH}}-C(O)-O^\ominus\ Na^\oplus$$
Epoxy succinic acid sodium salt

| heat
V $$CH_3(CH_2)_{11}(CH_2CH_2O)_7CH_2-CH(OH)-C(O)-O^\ominus\ Na^\oplus$$
$$\phantom{CH_3(CH_2)_{11}(CH_2CH_2O)_7CH_2-}|$$
$$\phantom{CH_3(CH_2)_{11}(CH_2CH_2O)_7CH_2}C(O)-O^\ominus\ Na^\oplus$$

The compounds of the present invention are very good ingredients in a variety of applications due to the presence of both the two carboxyl groups. These applications include:

(a) emulsion polymerization;

(b) urethane foams as modifiers of bubble structure;

(c) pigment dispersion agents for hydrophobic pigments;

(d) personal care applications for excellent skin feel.

They are outstanding emulsifiers and wetting agents.

Preferred Embodiments

In a preferred embodiment s is 3.

In a preferred embodiment s is 5.

In a preferred embodiment s is 7.

In a preferred embodiment s is 9.

In a preferred embodiment s is 11.

In a preferred embodiment s is 13.

In a preferred embodiments is 16.

In a preferred embodiment x ranges from 3 to 10.

In a preferred embodiment y ranges from 1 to 10.

In a preferred embodiment s is 11 and x ranges from 3 to 10.

In a preferred embodiment s is 13 and x ranges from 3 to 10.

In a preferred embodiment s is 15 and x ranges from 3 to 10.

EXAMPLES

Raw Materials

Expoxy Succinic Acid

U.S. Pat. No. 4,065,475 to Hosi et al issued in December of 1977 discloses a process for preparation of cis epoxy succinic acid, a raw material for the preparation of the compounds of the present invention.

Epoxy succinic acid conforms to the following structure:

$$HO-(O)C-CH-CH-C(O)-OH$$

and is commercially available from a variety of sources.

Non-ionic Surfactants

The non-ionic surfactants useful as intermediates for the preparation of the compounds present invention are commercially available from Siltech LLC, Dacula Ga.

They conform to the following structure:

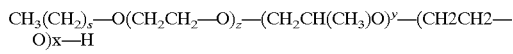

$$CH_3(CH_2)_s-O(CH_2CH_2-O)_z-(CH_2CH(CH_3)O)^y-(CH2CH2-O)x-H$$

s is an integer ranging from 3 to 21;

x, y and z are integers and are independently ranging from 0 to 20.

| Example | s | x | y | z |
|---|---|---|---|---|
| 1 | 3 | 5 | 0 | 0 |
| 2 | 5 | 10 | 0 | 0 |
| 3 | 7 | 6 | 1 | 10 |
| 4 | 9 | 1 | 0 | 0 |
| 5 | 11 | 0 | 0 | 10 |
| 6 | 17 | 0 | 0 | 10 |
| 7 | 3 | 0 | 0 | 0 |
| 8 | 5 | 10 | 1 | 20 |
| 9 | 9 | 15 | 20 | 5 |
| 10 | 11 | 20 | 3 | 10 |
| 11 | 17 | 20 | 20 | 20 |
| 12 | 21 | 1 | 10 | 20 |

Preparation of the Products of The Present Invention

General Procedure

Into a suitable vessel equipped with thermometer, agitation and heating capabilities is added the 648.0 grams of 25% sodium methylate in methanol. Next the specified amount of nonionic is added under good agitation. Next add 132.0 the epoxy succinic acid. Allow to mix until homogeneous. The exotherm is watched so that the temperature does not exceed 95° C. After the addition is complete the reaction mass is held at between 80–90° C. for four hours. During that time the % epoxide becomes vanishingly low.

Examples 13–24

Example 13

Into a suitable vessel equipped with thermometer, agitation and heating capabilities is added 648 grams of 25% sodium methylate in methanol. Next add 391.0 grams of nonionic (Example 1) and 132 grams of epoxy succinic acid under good agitation. The exotherm is watched so that the temperature does not exceed 95° C. After the addition is complete the reaction mass is held at between 80–90° C. for four hours. During that time the % epoxide becomes vanishingly low.

Example 14–24

Example 13 is repeated, only this time the specified quantity and type of nonionic is added replacing the quantity and type in example 13.

| | Non-ionic | |
|---|---|---|
| Example | Example | Grams |
| 13 | 1 | 391.0 |
| 14 | 2 | 639.0 |
| 15 | 3 | 990.0 |
| 16 | 4 | 299.0 |
| 17 | 5 | 723.0 |
| 18 | 6 | 807.0 |
| 19 | 7 | 171.0 |
| 20 | 8 | 1578.0 |
| 21 | 9 | 2315.0 |
| 22 | 10 | 1780.0 |
| 23 | 11 | 3307.0 |
| 24 | 12 | 2567.0 |

The compounds of the present invention can be placed into aqueous solution by adding enough water to bring the solids to between 20–60% solids. The preferred range is 30–40% solids. The products are used without purification.

APPLICATIONS

The products of the present invention are useful in:

(a) emulsion polymerization—The compounds are used at very low concentrations resulting in less water blush. A problem well known to those skilled in the emulsion polymer art.

(b) personal care applications (for excellent skin feel)— The products of the present invention have a very lubricious feel on the skin.

(c) Personal care applications (as detergents)—The compounds provide copious foam and are mild detergents. They do not sting and are non-irritation.

(d) Personal cars applications (liposomes)—finally, the compounds find applications in the formation of liquid crystals and liposomes in personal care applications.

What is claimed is:

1. A compound conforming to the following structure

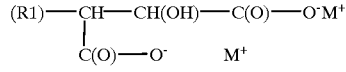

$$(R1)-CH-CH(OH)-C(O)-O^-M^+$$
$$\;\;\;\;\;\;\;\;\;|$$
$$\;\;\;\;\;\;\;C(O)-O^-\;\;\;\;M^+$$

wherein;

$R^1$ is $CH_3(CH_2)_s-O-(CH_2CH_2-O)_z-(CH_2CH(CH_3)O)_y-(CH_2CH_2-O)_x$;

s is an integer ranging from 3 to 21;

x, y and z are independently integers ranging from 0 to 20 with the proviso that x+y+z equal at least 1;

M is selected from the group consisting of H, Na, K, Li, and $NH_4$.

2. A compound of claim 1 wherein s is 3.

3. A compound of claim 1 wherein s is 5.

4. A compound of claim 1 wherein s is 7.

5. A compound of claim 1 wherein s is 9.

6. A compound of claim 1 wherein s is 11.

7. A compound of claim 1 wherein s is 13.

8. A compound of claim 1 wherein s is 17.

9. A compound of claim 1 wherein s is 19.

10. A compound of claim 1 wherein s is 21.
11. A compound of claim 1 wherein x ranges 3 to 10.
12. A compound of claim 1 wherein y ranges from 1 to 10.
13. A compound of claim 1 wherein x, y, and z are each 1 to 20.
14. A compound of claim 13 wherein s is 3.
15. A compound of claim 13 wherein s is 5.
16. A compound of claim 13 wherein s is 7.
17. A compound of claim 13 wherein s is 9.
18. A compound of claim 13 wherein s is 11.
19. A compound of claim 13 wherein s is 13.

* * * * *